United States Patent
McGhin et al.

(10) Patent No.: US 8,122,882 B2
(45) Date of Patent: Feb. 28, 2012

(54) RAINOUT REDUCTION IN A BREATHING CIRCUIT

(75) Inventors: Cary E. McGhin, Sugar Hill, GA (US); Robert L. Snyder, Suwanee, GA (US)

(73) Assignee: Smiths Medical ASD, Inc., Rockland, MA (US)

( * ) Notice: Subject to any disclaimer, the term of this patent is extended or adjusted under 35 U.S.C. 154(b) by 1156 days.

(21) Appl. No.: 11/926,990

(22) Filed: Oct. 29, 2007

(65) Prior Publication Data
US 2009/0107496 A1   Apr. 30, 2009

(51) Int. Cl.
*F24J 3/00* (2006.01)
*A61M 16/00* (2006.01)
*A61M 16/10* (2006.01)
*A62B 7/00* (2006.01)
*H05B 3/00* (2006.01)

(52) U.S. Cl. ......... 128/204.17; 128/203.27; 128/203.26; 128/203.17; 128/203.16; 128/203.12; 128/200.24

(58) Field of Classification Search ............. 128/200.24, 128/201.13, 204.18, 204.21, 203.12, 203.16, 128/203.17, 203.26, 203.27, 204.17; 239/338, 239/102.1, 102.2; 261/DIG. 65, 129, 154; 122/4 A, 5.5 A, 7 B, 13.01, 13.3–19.2, 33, 122/487, DIG. 7; 219/497, 505, 481, 496, 219/501

See application file for complete search history.

(56) References Cited

U.S. PATENT DOCUMENTS

| | | | |
|---|---|---|---|
| 4,232,667 A * | 11/1980 | Chalon et al. | 128/203.26 |
| 4,708,831 A * | 11/1987 | Elsworth et al. | 261/130 |
| 4,967,744 A * | 11/1990 | Chua | 128/204.18 |
| 5,392,770 A | 2/1995 | Clawson et al. | |
| 5,537,996 A * | 7/1996 | McPhee | 128/204.17 |
| 5,558,084 A | 9/1996 | Daniell et al. | |
| 5,943,473 A | 8/1999 | Levine | |
| 5,943,743 A | 8/1999 | Andersen | |
| 6,078,730 A * | 6/2000 | Huddart et al. | 392/480 |
| 6,662,802 B2 | 12/2003 | Smith et al. | |
| 6,918,389 B2 | 7/2005 | Seakins et al. | |
| 6,988,497 B2 | 1/2006 | Levine | |
| 7,061,252 B2 | 6/2006 | Bouton et al. | |
| 7,106,955 B2 | 9/2006 | Thudor et al. | |
| 7,120,354 B2 | 10/2006 | Mackie et al. | |
| 7,140,367 B2 | 11/2006 | White et al. | |
| 7,438,745 B2 * | 10/2008 | Deane et al. | 95/96 |
| 7,722,016 B2 | 5/2010 | Bradley et al. | |

(Continued)

FOREIGN PATENT DOCUMENTS

WO     97/18001 A1     5/1997

(Continued)

OTHER PUBLICATIONS

Manual for Fisher & Paykel Model Nos. MR700, MR720, MR730 Respiratory Humidifiers (Mar. 1998) (48 pages).

(Continued)

*Primary Examiner* — Annette Dixon
(74) *Attorney, Agent, or Firm* — Wood, Herron & Evans, LLP

(57) ABSTRACT

A breathing circuit includes inspiratory and expiratory limbs, each having a respective electrically energizable heating circuit. The heating circuits are independently and selectively electrically energized through separate power circuits such as to control the temperature in each limb in a desired fashion so as to reduce rainout in the breathing circuit and particularly in the expiratory limb.

24 Claims, 2 Drawing Sheets

U.S. PATENT DOCUMENTS

| | | | |
|---|---|---|---|
| 7,777,635 B2 | 8/2010 | Liu et al. | |
| 7,870,857 B2 * | 1/2011 | Dhuper et al. | 128/203.25 |
| 7,983,542 B2 | 7/2011 | McGhin et al. | |
| 8,011,071 B2 | 9/2011 | O'Brien | |
| 8,049,143 B2 | 11/2011 | Andel et al. | |
| 8,059,947 B2 | 11/2011 | Bradley et al. | |
| 2002/0083947 A1 | 7/2002 | Seakins | |
| 2002/0124847 A1 | 9/2002 | Smith et al. | |
| 2003/0079748 A1 | 5/2003 | Seakins | |
| 2003/0154977 A1 | 8/2003 | White et al. | |
| 2004/0118401 A1 | 6/2004 | Smith et al. | |
| 2004/0250815 A1 | 12/2004 | Scott et al. | |
| 2007/0051368 A1 | 3/2007 | Seakins et al. | |
| 2008/0028850 A1 | 2/2008 | Payton et al. | |
| 2008/0054497 A1 | 3/2008 | Bradley et al. | |
| 2008/0054500 A1 | 3/2008 | Bradley et al. | |
| 2009/0065002 A1 | 3/2009 | Hunt et al. | |
| 2009/0107493 A1 | 4/2009 | Liu et al. | |
| 2009/0107981 A1 | 4/2009 | Andel et al. | |
| 2009/0107982 A1 | 4/2009 | McGhin et al. | |
| 2009/0110022 A1 | 4/2009 | Snyder et al. | |
| 2009/0110029 A1 | 4/2009 | Bradley et al. | |

FOREIGN PATENT DOCUMENTS

| | | |
|---|---|---|
| WO | 2006/127257 A2 | 11/2006 |

OTHER PUBLICATIONS

Technical Manual Fisher & Paykel Respiratory Humidifier Model Nos. MR700, MR720, MR730, MR 480 (Mar. 2001) (64 pages).
Allegiance Healthcare 510K No. K993833 for Airlife® Heated Ventilator and Anesthesia Breathing Circuits (5 pages) (Dec. 10, 1999).
Brochure for Hudson RCI Humid-Heat® (6 pages).
Operating Manual for Fisher & Paykel Model Nos. MR700, MR720, MR730 Respiratory Humidifiers (Mar. 1994) (46 pages).
Instruction Sheet for Airlife® Single Heated Adult Respiratory Circuit (2 pages) (date uncertain).
Cardinal Health RT110 Data for Circuits, reprinted from the internet Jun. 3, 2006 (2 pages).
Fisher & Paykel 900MR561 Temperature Probe Label (one page) (date uncertain).
Fisher & Paykel Airway Temperature Probes Instructions for Use (3 pages) (2003).
Cat. RT110 Insert for Airlife™ Adult Respiratory Circuit—Heated (one page) (undated).
Extended European Search Report in counterpart European Application No. 08167297.4-2320 dated Mach 9, 2009 (5 pages).
Technical Manual for Fisher & Paykel Respiratory Humidifier Model No. MR850, Revision J, copyright 2005, (62 pages).

* cited by examiner

RAINOUT REDUCTION IN A BREATHING CIRCUIT

FIELD OF THE INVENTION

The present invention relates to a respiratory apparatus and in particular to the reduction of condensation, or rainout, in the limbs of a respiratory breathing circuit, and more particularly to reduction of rainout in the expiratory limb of such a breathing circuit.

BACKGROUND OF THE INVENTION

Respiratory systems provide breathable gas, such as oxygen, anesthetic gas and/or air directly to a patient's mouth, nose or airway to assist or facilitate breathing by the patient. A ventilator may be used as part of the respiratory system to drive the breathable gas to the patient through an inspiratory limb hose or conduit of a breathing circuit. An expiratory limb hose or conduit of the breathing circuit is provided to carry expelled air and other gas(es) from the patient back to the ventilator.

It is typically desired to warm and impart humidity to the breathable gas before it is provided to the patient. For that purpose, many respiratory systems include a humdificiation system having a chamber for holding water and a heater unit to which the chamber may be releasably mounted. The heater unit includes a heater, which may be comprised of one or more heating elements and a metal plate defining a hot plate. A wall of the chamber, such as the bottom surface of the chamber, is thermally conductive and in thermal contact with the hot plate of the heater, to thus heat the water in the chamber. The chamber may be manually refillable, or there may be a water source to selectively fill the chamber as it empties. The breathable gas is coupled to the chamber and is passed through the chamber to be heated and humidified. Examples of heater unit and chamber arrangements are shown in U.S. Pat. Nos. 6,988,497 and 5,943,473. The inspiratory limb carries the heated and humidified gas to the patient and the expiratory limb carries exhaled air and possibly other gases from the patient.

As the gas(es) travel to and from the patient along the elongated hoses or conduits of the inspiratory and expiratory limbs, respectively, they tend to cool such that condensation can form in the limbs. This condensation, referred to as rainout, can present serious and sometimes severe hazards. When present, the rainout must be carefully drained and handled. To reduce the incidence of rainout in the inspiratory limb, a heater circuit is provided to add heat to the heated and humidified gas passing through that limb to the patient. The heater circuit may be in the form of one or more elongated, and possibly coiled, heater wires running along the limb, such as through the interior of the limb. The temperature of the gas at the patient, such as at the outlet of the inspiratory limb, is measured, and a power circuit is operated to control the heater circuit in an effort to add heat as necessary to achieve a desired or set point temperature of the gas thereat.

Typically, the set point is selected to be above the outlet temperature of the chamber. Also, by heating the gas as it passes through the inspiratory limb, the incidence of rainout can be reduced. Where an expiratory limb is also provided, however, cooling of the expelled gas(es) passing through that limb increases the incidence of rainout in the expiratory limb. Hence, the expiratory limb may also include a heater circuit coupled to the power circuit so that the gas(es) passing through the expiratory limb is also heated. Heating the expiratory limb advantageously helps reduce rainout in the expiratory limb. An example of a breathing circuit with heated limbs is shown in U.S. Pat. No. 6,078,730.

The heater circuits of the two limbs may be substantially identical, such that the temperature in each limb is being driven to the same internal temperature. However, undesirable levels of rainout might still occur in the expiratory limb because the inspiratory limb is being controlled to deliver a specific airway temperature. Accumulation of fluid in the expiratory circuit as a result of such rainout can cause increased expiratory resistance and lead to unintentional lavage or fluid overload of the patient's lungs. Expiratory limb rainout may be further reduced by maintaining a higher temperature in the expiratory limb than in the inspiratory limb, such as an offset or temperature differential of 4 to 5 degrees Celsius. To achieve such a temperature differential, it is proposed to use different watt density heater wire in one limb than is used in the other limb. As a result, operation of the power circuit results in different levels of heating within the respective limbs aimed at maintaining a fixed temperature differential therebetween. Using different watt density wires for the respective limbs thus has advantages, but not without drawbacks. For example, use of different watt density wires creates inventory and manufacturing issues. Further, the range of operating temperatures in the two limbs may be limited.

SUMMARY OF THE INVENTION

The present invention provides an apparatus and method for effectively reducing rainout in a breathing circuit, and particularly in an expiratory limb thereof, which overcomes drawbacks normally associated with using different watt density wires for the respective limbs of a breathing circuit. To that end, and in accordance with the principles of the present invention, the inspiratory and expiratory heating circuits are selectively electrically energized by separate power circuits each operated independently of the other. More particularly, a processor is adapted to not only control a power circuit for the inspiratory limb in response to the measurement of the gas temperature at the patient, but to also independently control another power circuit for the expiratory limb to thereby provide flexibility in varying the level of heat input to the expiratory limb.

With the independent operation possible with the present invention, the limbs may use substantially identical heating circuits, such as by using the same watt density heater wire for each, thereby simplifying inventory and manufacture. Additionally, the offset or temperature differential between the limbs may be modified without changing the limbs or the heating circuits thereof and without being otherwise limited in dependence on the ability to control the temperature of the inspiratory limb. The present invention thus also increases the range of operation of the temperatures in the two limbs, irrespective of whether the heating circuits are substantially identical.

By virtue of the foregoing there is thus provided an apparatus and method for effectively reducing rainout in a breathing circuit, and particularly in an expiratory limb thereof, which overcomes drawbacks normally associated with using different watt density wires for the respective limbs of a breathing circuit. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate an embodiment of the invention and, together with the general description of the invention given above and the detailed description of the embodiment given below, serve to explain the principles of the present invention.

DETAILED DESCRIPTION OF DRAWINGS

Figure 1:
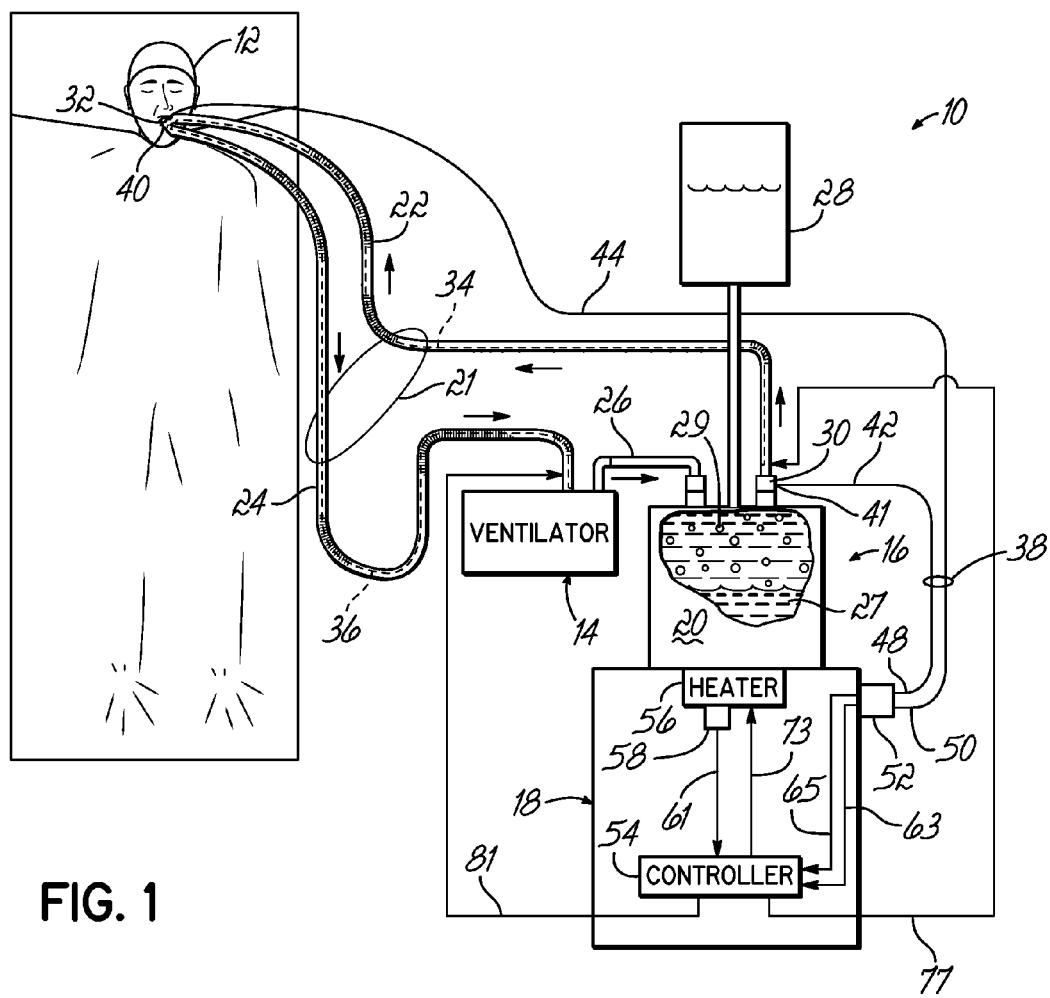
FIG. 1 is a diagram of a respiratory system embodying principles of the present invention.

FIG. 1 is an exemplary respiratory system 10 for supplying breathable gases to a patient 12. In the illustrated embodiment, the respiratory system 10 includes a ventilator 14, a humidification system 16 having a heater unit 18, a heatable container for water such as a disposable chamber 20, and a breathing circuit 21 having a first elongated hose or conduit 22 defining an inspiratory limb 22 and a second elongated hose or conduit 24 defining an expiratory limb 24. Ventilator 14 drives breathable gas, such as oxygen, anesthetic gas and/or air, through gas conduit 26 and into an air inlet of chamber 20. Water 27 is received in chamber 20, either by being poured in manually or automatically from a water supply 28 such as a bag or bottle, and which may be vented. Chamber 20 is heated by heater unit 18 to heat up the water 27 therein. Heated water vapor 29 may also be produced within chamber 20 above the level of water 27 therein. The gas from conduit 26 passes over or through the heated water 27 and/or through heated water vapor 29 to become heated and humidified before exiting the chamber 20 as heated and humidified gas. Examples of humidification systems are shown in aforementioned U.S. Pat. Nos. 6,988,497 and 5,943,473, 7,722,016, and U.S. Pat. Publication No. 2008/0054497, the disclosures of all four of which are incorporated herein by reference in their entireties.

The heated and humidified gas flows from chamber 20 to the patient 12 by passing through inspiratory limb 22. A first end of inspiratory limb 22 is coupled to chamber 20 by a connecting member or joint 30, and a second end of inspiratory limb 22 is coupled to a breathing attachment 32 that facilitates delivery of the gas passed therethrough to the patient 12. The breathing attachment 32 may couple to an invasive apparatus such as an endotracheal tube, or a non-invasive apparatus such as a mask (both not shown) that promotes gas delivery. The gas may be further heated while passing through inspiratory limb 22 to breathing attachment 32 by heater circuit 34 associated with inspiratory limb 22. Expiratory limb 24 allows exhaled air and other gas expelled from patient 12 to pass back to ventilator 14, the atmosphere or elsewhere. Another heater circuit 36 is associated with expiratory limb 24 for heating the expelled gas. In the embodiment shown herein, heater circuit 34 and heater circuit 36 are substantially identical, each being comprised of one or more elongated heater wires having the same specific watt density(ies). Alternatively, the watt density of the heater wire(s) of heater circuit 34 could be different from the watt density of the heater wire(s) of heater circuit 36. Further alternatively, different types of heater circuits or wire configurations could be employed for heater circuit 34 and/or 36.

Respiratory system 10 also includes a patient temperature cable (PTC) 38 having one or more temperature responsive devices such as thermistor-containing probes as at 40, 41 to provide thermal feedback in the form of temperature readings to heater unit 18 for purposes to be described. Temperature cable 38 includes a first communication cable 42 and a second communication cable 44. Temperature probe 41 is coupled to joint 30 at the entry to inspiratory limb 22 to provide a temperature reading via first communication cable 42 indicative of the actual measured temperature of the heated and humidified gas exiting from chamber 20 ("the output temperature"). Temperature probe 40 is coupled to breathing attachment 32 such as at the exit of inspiratory limb 22 to provide a temperature reading via second communication cable 44 indicative of the actual measured temperature of the humidified gas being provided to the patient ("the patient temperature"). First communication cable 42 has an end 48 electrically coupled to heater unit 18 to communicate the output temperature to heater unit 18. Similarly, second communication cable 44 has an end 50 electrically coupled to heater unit 18 to communicate the patient temperature to heater unit 18. Ends 48 and 50 may be advantageously secured together through a connector 52 to facilitate coupling the first and second cables 42, 44 to a mating socket (not shown) on heater unit 18. Further details of a suitable cable 38 and probes 40, 41 are set out in U.S. Pat. No. 8,059,947 and U.S. Pat. Publication No. 2009/0110029, the disclosures of both of which are incorporated herein in their entirety by reference.

Heater unit 18 includes a controller 54 and a heater 56. Thermally coupled to heater 56 is a temperature responsive device 58 such as a thermistor to provide readings of the actual measured temperature of heater 56 to controller 54 ("the input temperature"). The input temperature is representative of the heat input to the chamber 20, and may be used as a heat input value. An example of one suitable heater 56 is described in U.S. Pat. No. 8,049,143, the disclosure of which is incorporated herein by reference in its entirety. The output temperature readings and the patient temperature readings are also coupled to controller 54, and are utilized as appropriate for controlling heater 56 and heater circuits 34 and 36 as will be described below.

Figure 2:
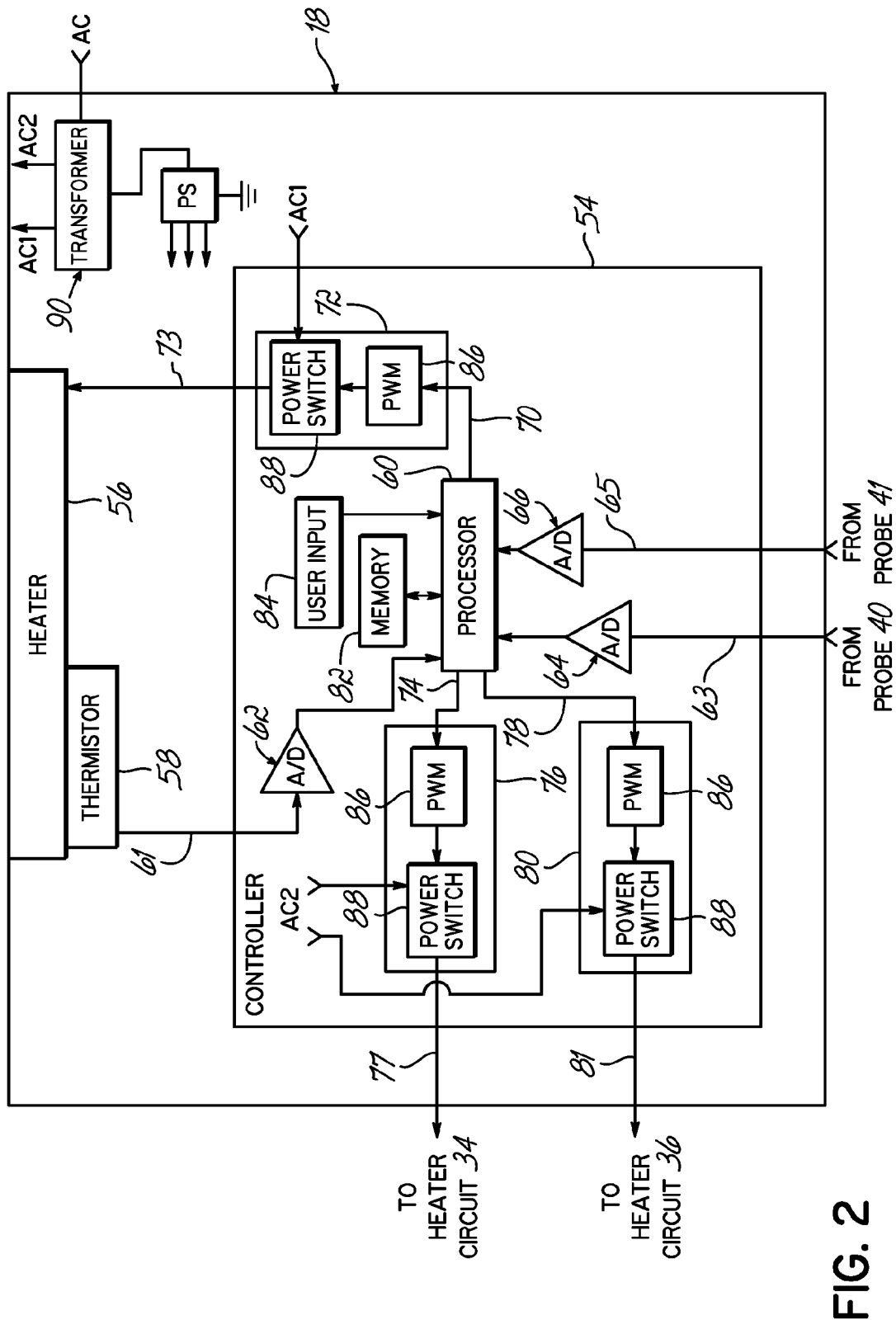
FIG. 2 is a schematic diagram of the heater unit of FIG. 1.

As seen in greater detail in FIGS. 2, controller 54 includes a processor 60, which may be a microprocessor or other computer or programmable logic device, which is operatively associated with probes 40 and 41, temperature responsive device 58, heater 56, and heater circuits 34 and 36. The input temperature readings from temperature responsive device 58 are communicated to processor 60 as at 61 via A/D converter 62. The patient temperature readings from probe 40 are communicated to processor 60 as at 63 via A/D converter 64. The output temperature readings from probe 41 are communicated to processor 60 as at 65 via A/D converter 66. Processor 60 outputs a heater control signal as at 70 to control a power circuit 72 to selectively electrically energize heater 56, as at 73, for regulating the temperature thereof so as to control heating of water 27 in chamber 20. Processor 60 outputs an inspiratory control signal as at 74 to control a power circuit 76 to selectively electrically energize heating circuit 34, as at 77 for regulating the heat input to gas passing through inspiratory limb 22. Processor 60 outputs an expiratory control signal as at 78 to control a power circuit 80 to selectively electrically energize heating circuit 36, as at 81, for regulating the heat input to gas(es) passing through expiratory limb 24. Processor 60 operates under programs or algorithms stored in a memory 82 and in response to data input via a user input 84. Processor 60 advantageously utilizes PID feedback control for generating the control heater, inspiratory and expiratory control signals as described in U.S. Pat. No. 7,983,542, the disclosure of which is incorporated herein by reference in its entirety.

Each power control circuit includes a control circuit such as a pulse width modulator ("PWM") circuit 86 and a power switch 88, such as a triac or the like, so as to regulate the amount of AC power coupled therethrough, such as from one or more taps AC1 and AC2 of a transformer 90 in relation to the control signal (70, 74 or 78) whereby to selectively electrically energize the respective heater 56, heater circuit 34 or heater circuit 36. PWM circuit 86 may modulate power switch 88 either by turning it on and off or by varying its conductance as desired whereby to provide the desired selective energization in a manner intended to desirably heat and humidify gas passing through chamber 20 and/or limbs 22 and 24. Signals 70, 74 and 78 can each be independently developed by processor 60, and operable for managing separate power circuits 72, 76 and 80, respectively. In the embodiment shown, breathing circuit 21 is heated, such that processor 60 is adapted to regulate the temperature of heater 56 and of limbs 22 and 24 in relation to a desired or set point temperature for the patient temperature. Heater 56 is regulated in relation to that set point temperature as described in aforesaid U.S. Pat. No. 7,983,542, wherein the correction signal C generated thereby is used as the heater control signal 70 for power circuit 72. The PID feedback control thereof may also be implemented to generate a correction signal C for use as the inspiratory control signal 74 for power circuit 76. As the heater circuit 36 of expiratory limb 24 is responsive to a separate power circuit 80 from that of heating circuit 34 of inspiratory limb 22, processor 60 is adapted to provide an independent expiratory control signal 78 for power circuit 80.

In one embodiment, expiratory control signal 78 may be a multiple of inspiratory control signal 75 based on a scaling factor selected or programmed to match the desired temperature differential between limbs 22 and 24. The scaling factor could be a preset multiplier determined empirically for the design of the components involved based on a pres-set temperature differential, or a variable scaling factor based on a range of available temperature differentials which may be selected by a user (not shown) through user input 84, with the scaling factor(s) being stored as control data in memory 82. Alternatively, a plurality of scaling factors could be determined empirically for the design of the components involved in relation to the estimated flow rate or flow rate band in current use of system 10, and the appropriate scaling factor utilized based on the flow rate or flow rate band involved, and further in relation to the selected or preset temperature differential. To that end, the flow rate of gas through chamber 20, and thus limb 22, may vary from 1 or 2 liter per minute (1 pm) to between 50 and 100 1 pm, usually within 2 1 pm to 70 1 pm. Temperature responsiveness of system 10 is different in relation to the flow rate. In one embodiment, three flow rate bands are selected, such as a low flow rate band of 5 1 pm or less, a high flow rate band of 10 1 pm or greater, and an intermediate flow rate band between 5 and 10 lpm, each with its own respective scaling factor. A warm-up process and/or a steady state process can be implemented as described in aforesaid U.S. Pat. No. 7,983,542, such that the likely flow rate band is determinable. That information can be used by processor 60 to select the appropriate scaling factor for generating expiratory control signal 78 in relation to inspiratory control signal 74.

Alternatively, a desired temperature of limb 24 may be attempted based on temperature readings such as the patient temperature or other temperature readings such as from expiratory limb 24 for generating expiratory control signal 78 much the same as inspiratory control signal 74 is generated. The desired temperature could be selected in its own right, or by selection of a desired temperature differential in relation to the set point for the patient temperature.

Presence of heated breathing circuit 21 may be indicated via the user input 84 or may be automatically detected as described in U.S. Pat. Publication No. 2009/0107982, the disclosure of which is incorporated herein by reference in its entirety. Heater unit 18 may also include a power supply (PS) to provide one or more regulated DC voltage levels for use in powering the various aspects of controller 54. Heater 56 and heater circuits 34, 36 may be powered with AC power through taps AC1 and AC2 of transformer 90, and power supply PS may obtain its power from transformer 90 as well. Heater 56 could, alternatively obtain power from the AC source powering transformer 90. Heater unit 18 may also include one or more displays, input controls such as buttons and dials or the like, and alarm indicators (all not shown), and may further have various interface inputs and outputs such as to couple to a source of AC power (not shown) and to the heater circuits 34, 36, and PTC cable 38. As will be appreciated, while the various devices of controller 54 are shown as being separately coupled to processor 60, they may communicate over one or more common busses. Also, one or more of power switches 88 may be mounted on heat sinks or the like (not shown) separate from the rest of the circuitry of controller 54.

Controller 54 may also include various control and power management functions. Further, heater unit 18 may be mounted with a self-aligning lock mount (also not shown). Various of the foregoing are shown in U.S. Pat. Nos. 7,777, 635, and 8,011,071; and U.S. Publication Nos. 2009/ 0110022, 2009/0107981, and 2009/0107493; the disclosures of all five of which are incorporated herein by reference in their entireties.

In use, with breathing circuit 21 being heated by heater circuits 34 and 36, processor 60 is adapted to independently provide inspiratory and expiratory control signals 74 and 78, for use by separate power circuits 76 and 80 so as to independently regulate heat input to limbs 22 and 24. As a result, heat input to expiratory limb 24 may be independently regulated, so as to adjust the temperature of expiratory limb 24 without necessarily impacting the temperature of inspiratory limb 22. Hence, processor 60 may provide critical control over the temperature of inspiratory limb 22 while also affording independent control over the temperature of expiratory limb 24. As a consequence, heating circuits 34 and 36 may be substantially identical, such as by using the same watt density heater wire(s) for each, thereby simplifying inventory and manufacturing. Additionally, the offset or temperature differential between limbs 22 and 24 may be modified without changing either or both of limbs 22, 24 or heating circuits 34, 36 thereof and without being otherwise limited in dependence on the ability to control the temperature of inspiratory limb 22. The present invention thus also increases the range of operation of the temperatures in limbs 22 and 24, irrespective of whether the heating circuits are substantially identical.

By virtue of the foregoing, there is thus provided an apparatus and method for effectively reducing rainout in a breathing circuit, and particularly in an expiratory limb thereof, which overcomes drawbacks normally associated with using different watt density wires for the respective limbs of a breathing circuit.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. While the power circuits 72, 76 and 80 are shown as being comprised of a PWM circuit 86 and a power switch 88, other configurations and arrangements are possible. By way of example, an opto-isolator (not shown) may be provided to isolate PWM Circuit 86 from processor 60. By way of further example, the power circuit could include only a power switch, such as power switch 88, such that any other circuitry provided for controlling switch 88 not being considered part of the power circuit, and may even include direct (or isolated) control from processor 60. Additionally, while ventilator 14 is shown as driving the gas through chamber 20, it will be appreciated that other gas systems could be employed, such as from a hospital oxygen supply, a CPAP or BiPAP pump, or other air or oxygen pumping system. The invention in its broader aspects is therefore not limited to the specific details, representative apparatus and methods and illustrative examples shown and described. Accordingly, departures may be made from such details without departing from the scope or spirit of Applicants' general inventive concept.

Having described the invention, what is claimed is:

1. A method of reducing rainout in a breathing circuit having an inspiratory limb having an inlet adapted to receive a breathable gas and an outlet adapted to supply the breathable gas to a patient, the inspiratory limb including a first electrically energizable heater circuit extending substantially along the length of the inspiratory limb, and an expiratory limb with a second electrically energizable heater circuit extending substantially along the length of the expiratory limb, the method comprising:

coupling a heated and humidified breathable gas to the inlet of the inspiratory limb to be supplied to the patient from the outlet of the inspiratory limb such that the heated and humidified breathable gas passes along the length of the inspiratory limb between the inlet and the outlet; and independently, selectively electrically energizing the first and second heater circuits as the heated and humidified breathable gas passes along the length of the inspriratory limb.

2. The method of claim 1 further comprising selectively energizing the second heater circuit to heat the expiratory limb to a different temperature than the inspiratory limb.

3. The method of claim 2 further comprising selectively energizing the second heater circuit to heat the expiratory limb to a higher temperature than the inspiratory limb.

4. The method of claim 3 further comprising selectively energizing the second heater circuit to heat the expiratory limb to a temperature higher than the inspiratory limb based on a selected temperature differential.

5. The method of claim 2 further comprising selectively energizing the second heater circuit to heat the expiratory limb in scaled relation to selective energization of the first heater circuit.

6. The method of claim 1 further comprising selectively energizing the first heater circuit to maintain a temperature in the expiratory limb above a minimum temperature desired for the heated and humidified breathable gas.

7. The method of claim 1 further comprising selectively energizing the first heater circuit to maintain a user specified temperature in the inspiratory limb.

8. The method of claim 1 further comprising selectively energizing the first heater circuit to maintain a desired temperature in the inspiratory limb.

9. The method of claim 1 further comprising selectively energizing the second heater circuit to maintain a desired temperature in the expiratory limb.

10. The method of claim 1 further comprising selectively energizing the first heater circuit such that the temperature in the inspiratory limb is different than that in the expiratory limb.

11. A method of regulating heat input to a breathing circuit having an inspiratory limb having an inlet adapted to receive a breathable gas and an outlet adapted to supply the breathable gas to a patient and an expiratory limb, the method comprising;

coupling a heated and humidified breathable gas to the inlet of the inspiratory limb to be supplied to the patient from the outlet of the inspiratory limb such that the heated and humidified breathable gas passes along the length of the inspiratory limb; and selectively electrically energizing a first electrically energizable heater circuit associated with the inspiratory limb and independently selectively electrically energizing a second electrically energizable heater circuit associated with the expiratory limb.

12. In combination:

a breathing circuit including an inspiratory limb having a first electrically energizable heater circuit and an expiratory limb having a second electrically energizable heater circuit; and a controller having a first output operatively coupled to the first heater circuit and a second output operatively coupled to the second heater circuit, the controller adapted to independently provide the first and second outputs so as to independently and selectively electrically energize the first and second heater circuits.

13. The combination of claim 12, the controller including a first power circuit being selectively operable to selectively energize the first heater circuit and a second power circuit being selectively operable to selectively energize the second heater circuit, the first and second power circuits being independently operable whereby to independently and selectively electrically energize the first and second heater circuits.

14. The combination of claim 13 further comprising an electric power supply coupled to the first and second power circuits.

15. The combination of claim 13, the first and second power control circuits each including a respective power switch.

16. The combination of claim 13, the first and second power control circuits each further including a PWM circuit coupled to the respective power switches.

17. The combination of claim 12, the first and second heater circuits being substantially identical.

18. The combination of claim 12, the controller being adapted to selectively electrically energize at least one of the first and second heater circuits such that the temperature in the expiratory limb is different than in the inspiratory limb.

19. The combination of claim 18, the controller being adapted to selectively electrically energize at least one of the first and second heater circuits such that the temperature in the expiratory limb is greater than in the inspiratory limb.

20. The combination of claim 12, the controller being adapted to selectively electrically energize at least one of the first and second heater circuits such that the temperature in the expiratory limb differs from that in the inspiratory limb based on a selected temperature differential.

21. A controller for a humidification system having a first output adapted to be operatively coupled to a first heater circuit associated with an inspiratory limb of a breathing circuit and a second output adapted to be operatively coupled to a second heater circuit associated with an expiratory limb of said breathing circuit, the controller adapted to independently provide the first and second outputs whereby to independently and selectively electrically energize said first and second heater circuits of said breathing circuit.

22. The controller of claim 21 including a selectively operable first power circuit providing the first output and a selectively operable second power circuit providing the second output.

23. The controller of claim 22, the first and second power control circuits each including a respective power switch.

24. The controller of claim 23, the first and second power control circuits each further including a PWM circuit coupled to the respective power switches.

* * * * *